United States Patent
Ceddia et al.

(10) Patent No.: US 10,857,195 B2
(45) Date of Patent: Dec. 8, 2020

(54) PLANT EXTRACTS FOR IMPROVING SLEEP

(71) Applicant: Kemin Industries, Inc., Des Moines, IA (US)

(72) Inventors: Michael Ceddia, Ankeny, IA (US); Kelli Herrlinger, Johnston, IA (US); Brandon Lewis, Johnston, IA (US); Shulin Feng, West Des Moines, IA (US); Kristin Nieman, Mitchelville, IA (US)

(73) Assignee: KEMIN INDUSTRIES, INC., Des Moines, IA (US)

( * ) Notice: Subject to any disclaimer, the term of this patent is extended or adjusted under 35 U.S.C. 154(b) by 653 days.

(21) Appl. No.: 14/855,003

(22) Filed: Sep. 15, 2015

(65) Prior Publication Data

US 2016/0074459 A1 Mar. 17, 2016

Related U.S. Application Data

(60) Provisional application No. 62/050,563, filed on Sep. 15, 2014.

(51) Int. Cl.
*A61K 36/53* (2006.01)
*A61K 36/00* (2006.01)
*A61K 36/534* (2006.01)
*A61K 31/216* (2006.01)

(52) U.S. Cl.
CPC .......... *A61K 36/534* (2013.01); *A61K 31/216* (2013.01); *A61K 36/53* (2013.01)

(58) Field of Classification Search
None
See application file for complete search history.

(56) References Cited

U.S. PATENT DOCUMENTS

| | | | |
|---|---|---|---|
| 4,752,476 A * | 6/1988 | Copney | A61K 36/534 424/745 |
| 2014/0302170 A1* | 10/2014 | Jones | A61K 31/405 424/641 |

\* cited by examiner

*Primary Examiner* — Michael Barker
*Assistant Examiner* — Randall Winston
(74) *Attorney, Agent, or Firm* — Nyemaster Goode P.C.

(57) ABSTRACT

Extracts of plants of the Lamiaceae family, including the *Mentha* genus, are shown to have a positive impact on overall cognitive health, including improvements in memory, reasoning, attention/concentration, planning, mood, sleep and associated behaviors.

13 Claims, 2 Drawing Sheets

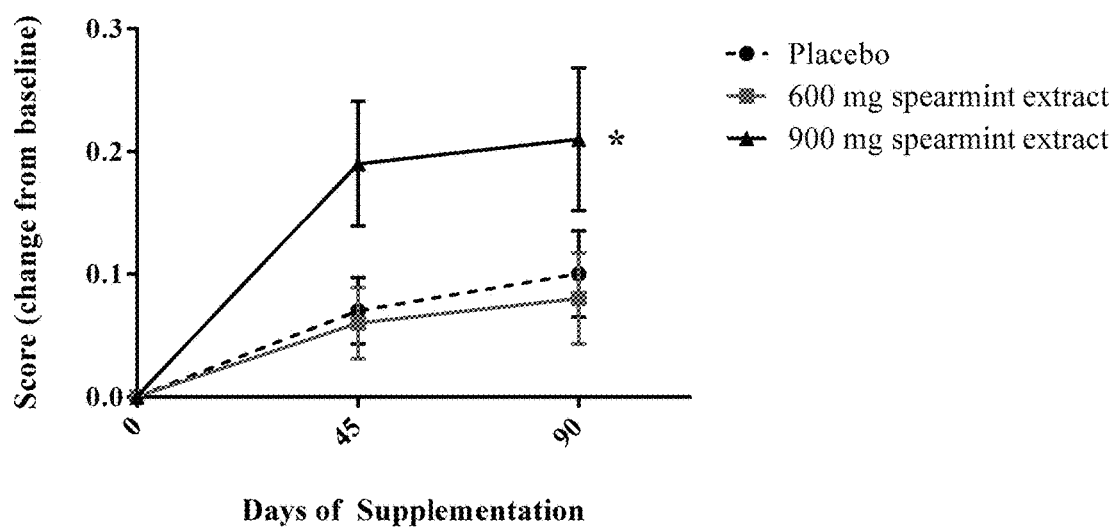
Figure 1. Quality of working memory scores after 90 days of spearmint supplementation. Data expressed as mean difference from baseline (day 0) for the daily averages ± standard error of the mean (n = 28-30/group).

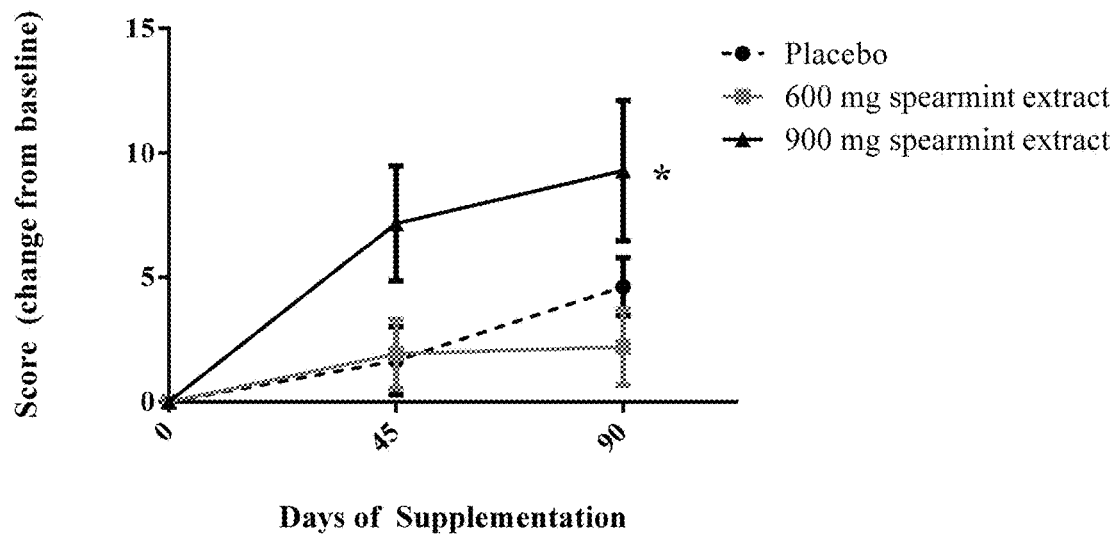
Figure 2. Spatial working memory distractor items correctly identified after 90 days of spearmint supplementation. Data expessed as mean difference from baseline (day 0) for the daily averages ± standard error of the mean (n = 28-30/group).

PLANT EXTRACTS FOR IMPROVING SLEEP

This application claims priority to U.S. Patent Application 62/050,563, filed Sep. 15, 2014, which is incorporated herein in its entirety by this reference.

BACKGROUND OF THE INVENTION

There is a strong demand for products that can improve cognitive health or function and the market for these products has continued to grow in recent years despite the unfavorable economic pressures. Some of this growth can be attributed to the growth of an aging population, which is especially true in Asia and the United States. Worldwide cognitive health ingredient sales are around $455 million. Frost and Sullivan have predicted an annual growth rate in this area to 12% from 2016 to 2019.

Major ingredients for cognitive health currently include phosphatidylserine (PS), CoQ10, omega-3 (marine oils/algae oils), citicoline, ginko and *ginseng*. Of the largest cognitive health ingredients, phosphatidylserine is the only one with FDA approved qualified claim. With increasing scientific evidence to support the claim, the ingredient has been enjoying double digit growth in sales. In 2010, DHA and EPA health claims for brain function, heart health and vision obtained a positive opinion from EFSA in Europe. Citicoline is promoted as an ingredient that prevents neuronal degeneration and improves memory.

Decreased sleep quality has been correlated with cognitive decline in the aged (Blackwell T, Yaffe K, Laffan A, Ancoli-Israel S, Redline S, Ensrud K E, et al. Associations of objectively and subjectively measured sleep quality with subsequent cognitive decline in older community-dwelling men: the MrOS sleep study. Sleep 2014; 37:655-663). In addition, increased oxidative stress and inflammation are documented in sleep deprivation (Lavie L. Oxidative stress in obstructive sleep apnea and intermittent hypoxia—revisited—the bad ugly and good: implications to the heart and brain. Sleep Med Rev 2015; 20:27-45). Limited studies are available showing benefit of melatonin, lemon balm, and valerian on sleep (C Cerny A, Schmid K. Tolerability and efficacy of valerian/lemon balm in healthy volunteers (a double-blind, placebo-controlled, multicentre study). Fitoterapia 1999; 70:221-228. Taavoni S, Nazem Ekbatani N, Haghani H. Valerian/lemon balm use for sleep disorders during menopause. Complement Ther Clin Pract 2013; 19:193-196).

Rosmarinic acid (RA) is one of the major components found in spearmint and is an important contributor to its antioxidant capacity (Fletcher et al. Heat stress reduces the accumulation of rosmarinic acid and the total antioxidant capacity in spearmint (*Mentha spicata* L). Journal of the Science of Food and Agriculture 85: 2429-2436, 2005). RA, a naturally occurring phenolic compound, is an ester of caffeic acid and 3,4-dihydroxyphenyllactic acid. Its structure consists of a carbonyl group, unsaturated double bond, and carboxylic acid between two phenolic rings. RA has shown several biological activities, such as anti-inflammatory, anti-mutagenic, antibacterial, antidepressant, HIV-1 inhibitory, antioxidant, and antiviral properties. These properties have made RA an attractive ingredient for the pharmaceutical and cosmetic industries. RA has been used topically in Europe as a non-steroidal anti-inflammatory drug (Ritschel et al. Percutaneous absorption of rosmarinic acid in the rat. *Methods and Findings in Experimental and Clinical Pharmacology* 11: 345-352, 1989). Due to its extensive use as a flavoring agent and preservative in the food industry, RA is regarded as a daily-consumed safe ingredient (Alkam et al. A natural scavenger of peroxynitrites, rosmarinic acid, protects against impairment of memory induced by Aβ25-35. *Behavioural Brain Research* 180: 139-145, 2007).

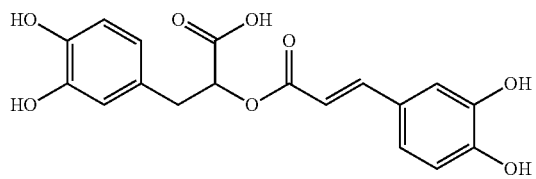

Rosmarinic acid

Evidence of RA's non-specific protective properties has been found within the brain. Improved anti-oxidant activity of the brain was demonstrated following administration of RA to aging mice which resulted in increased activities of superoxide dismutase (SOD) and catalase (CAT) in the brain, while decreasing malondialdehyde (MDA) (Shou et al. Rosmarinic acid attenuates D-galactose induced behavior impairment in mice and its mechanism. 2010, p. 1723-1726). These data demonstrate the non-specific protective properties of RA as an antioxidant; however, no previous data has demonstrated RA's ability to affect the brain in specific regions or on specific clinical outcomes.

In vivo, three studies previously evaluated administration of RA. These studies administered RA either orally or IP in intracranial injury models or a stress model that were used to represent specific cognitive disease states (Alkam et al. A natural scavenger of peroxynitrites, rosmarinic acid, protects against impairment of memory induced by Aβ25-35. *Behavioural Brain Research* 180: 139-145, 2007; Park et al. Subchronic administration of rosmarinic acid, a natural prolyl oligopeptidase inhibitor, enhances cognitive performances. *Fitoterapia* 81:644-648, 2010; Zhou et al. Rosmarinic acid attenuates D-galactose induced behavior impairment in mice and its mechanism. Intl Conf BMEI 4:1723-1726, 2010). Although RA showed benefit in these models, they were not validated models for evaluation of normal aging cognitive changes. In addition, it is unknown if the mechanisms of action were specific or non-specific due to antioxidant effects. Currently, there are no published human studies evaluating RA supplementation alone or through use of a spearmint extract.

Learning and memory can be divided into two main categories, declarative and procedural. Declarative has temporal, spatial and associative memory components. This relates to learning and memory that has a conscious component requiring attention and alertness. In humans this relates to the acquisition, recognition and memory of discrete events, places, people, and facts. Procedural learning and memory can be formed when a declarative memory task becomes routine or habitual and was measured in the current animal study through the lever press. This relates to learning and memory that does not have a conscious component, which in humans is a habit or skill, such a riding a bike. Declarative tasks are thought of as hippocampal initiated, while procedural tasks are primarily linked to the caudate regions of the brain.

Working memory pertains to the ability to use and manipulate information stored within short-term memory. Current evidence indicates that even in healthy individuals working memory decreases with age, beginning in early adulthood (Park et al. 2002; Salthouse 1991; Salthouse 1994), indicating that a longer period of time will be necessary to process and retrieve stored information. Wesnes et al. reported in healthy individuals (n=2282; 18-87 years of age), a decrease of roughly 10% per decade in working memory occurred after the age of 40 (Wesnes 2003). This decline in working memory reached approximately 22% in subjects 70-80 years of age.

Memory impairment may occur in healthy, elderly individuals, and is considered a normal consequence of aging. In older subjects (>50 years), Gallo et al. reported that self-reported memory impairment occurs at a rate of approximately 20% (Gallo J J, Morales K H, Bogner H R, Raue P G, Zee J, Bruce M L, Reynolds C F. Long term effect of depression care management on mortality in older adults: follow-up of cluster randomized clinical trial in primary care. BMJ 2013; 346:f2570). Interestingly, in a cross-sectional study of 17 general practice clinics serving 2,934 patients aged 65 and older, 23% of these individuals self-reported memory impairment upon prompting; however, only 18% (of the 23%) had consulted a physician for their memory problem (Waldorff F B, Rishoj S, Waldemar G. If you don't ask (about memory), they probably won't tell. *J Fam Pract* 2008; 57(1):41-4.). Cognitive decline is generally accepted as a natural consequence of aging; however, it significantly decreases quality of life (Grossi D, Postiglione A, Schettini B, Trojano L, Barbarulo A M, Guigliano V, Ambron E, Aiello A. Autobiographical recall training in elderly adults with subjective memory complaint: a pilot study. *Percept Mot Skills* 2007; 104(2):621-8). It is estimated that 5.4 million elderly Americans have cognitive impairment without dementia and roughly 12% of these individuals will develop dementia annually (Plassman B L, Langa K M, Fisher G G, Heeringa S G, Weir D R, Ofstedal M B, Burke J R, Hurd M D, Potter G G, Rodgers W L, Steffens D C, Mcardle J J, Willis R J, Wallace R B. Prevalence of cognitive impairment without dementia in the United States. *Ann Intern Med* 2008; 148(6):427-34). Although a number of treatments are available for dementia, this prominent health concern emphasizes a need to explore methods to increase, maintain, or reduce the decline in cognitive function that is associated with aging.

Cognitive deficits associated with aging of the brain may result from a number of factors including hypertension and vascular dysfunction, dietary intake, metabolic dysfunction, increased oxidative stress and inflammation, changes in neuronal transmission, and sleep disruption. (Harman 2006; Uranga, Bruce-Keller et al. 2010; Gorelick, Scuteri et al. 2011; Levine and Stadtman 2001; Morris 2012) Tissue levels of protein, lipid, and DNA/RNA oxidation increase with age as a result of both increased reactive oxygen species production and decreased antioxidant repair. (Levine and Stadtman 2001) Aging of the brain has also been associated with changes in cholinergic neuronal transmission. Specifically, reduced levels of acetylcholine (ACh) and dopamine transporters are well documented in the aging brain and more advanced stages of cognitive dysfunction (i.e., Alzheimer's disease). (Bartus, Dean et al. 1982; Terry and Buccafusco 2003) Inflammatory signaling has also been reportedly increased with aging and is associated with neuronal dysfunction including elevated levels of TNF-α, interleukin (IL)-1, and IL-6. (Tha, Okuma et al. 2000; Michaud, Balardy et al. 2013) In addition, sleep disturbances and decreased sleep quality have been correlated with cognitive decline in the aged. (Yaffe et al. 2014; Blackwell et al. 2011; Blackwell et al. 2014; Jelicic et al. 2002; Song et al. 2014).

Cognitive decline and brain aging occurs in most mammals and is commonly reported in companion animals, particularly cats and dogs. Cognitive decline that occurs with aging in companion animals, called cognitive dysfunction syndrome, is often characterized by behavioral changes including but not limited to disorientation, sleep-wake cycle disruptions, anxiety, activity level alterations, and learning and memory deficits that cannot be attributed to other clinical outcomes (Landsberg et al. 2012). Specifically, cognitive decline has been reported in aging dogs on tests of spatial memory, spatial attention, and executive function as early as middle age (Studzinksi et al. 2006; Milgram et al. 1994; Milgram et al. 1994; Tapp et al. 2003). For this reason, early identification and nutritional intervention to prevent cognitive decline in companion animals may support quality of life.

Traditional medicine has long used plant-based remedies to treat a number of ailments and, more recently, plant-based remedies such as Ginko *biloba* (Wesnes K A, Ward T, Mcginty A, Petrini O. The memory enhancing effects of a *Ginkgo biloba/Panax ginseng* combination in healthy middle-aged volunteers. *Psychopharmacology* (Berl) 2000; 152(4):353-61; Snitz B E, O'meara E S, Carlson M C, Arnold A M, Ives D G, Rapp S R, Saxton J, Lopez O L, Dunn L O, Sink K M, Dekosky S T. Ginkgo biloba for preventing cognitive decline in older adults: a randomized trial. JAMA 2009; 302(24):2663-70), ginseng (Wesnes 2008; Reay J L, Kennedy D O, Scholey A B. Single doses of *Panax ginseng* (G115) reduce blood glucose levels and improve cognitive performance during sustained mental activity. *J Psychopharmacol* 2005; 19(4):357-65; Kennedy D O, Haskell C F, Robertson B, Reay J, Brewster-Maund C, Luedemann J, Maggini S, Ruf M, Zangara A, Scholey A B. Improved cognitive performance and mental fatigue following a multi-vitamin and mineral supplement with added guarana (*Paullinia cupana*). *Appetite* 2008; 50(2-3):506-13), and guarana (Kennedy 2004; Haskell 2007) have been investigated in clinical trials for their potential in enhancing cognitive function in healthy volunteers. A recent meta-analysis of 13 randomized controlled trials suggests herbal medicines provide a small but consistent benefit relative to placebo and are just as effective as pharmaceutical interventions in improving cognitive function in subjects with dementia (May B H, Lit M, Xue C C, Yang A W, Zhang A L, Owens M D, Head R, Cobiac L, Li C G, Hugel H, Story D F. Herbal medicine for dementia: a systematic review. *Phytother Res* 2009; 23(4):447-59). Furthermore, several trials have been conducted suggesting that consumption of plants within the Lamiaceae (mint) family, including lemon balm (Kennedy D O, Scholey A B, Tildesley N T, Perry E K, Wesnes K A. Modulation of mood and cognitive performance following acute administration of *Melissa officinalis* (lemon balm). *Pharmacol Biochem Behav* 2002; 72(4):953-64), lavender (Moss M, Cook J, Wesnes K, Duckett P. Aromas of rosemary and lavender essential oils differentially affect cognition and mood in healthy adults. Int J Neurosci 2003; 113(1):15-38), sage (Tildesley N T, Kennedy D O, Perry E K, Ballard C G, Savelev S, Wesnes K A, Scholey A B. *Salvia lavandulaefolia* (Spanish sage) enhances memory in healthy young volunteers. *Pharmacol Biochem Behav* 2003; 75(3):669-74; Tildesley N T, Kennedy D O, Perry E K, Ballard C G, Wesnes K A, Scholey A B. Positive modulation of mood and cognitive performance following administration of acute doses of *Salvia lavandulaefolia* essential oil to healthy young volunteers. *Physiol Behav* 2005; 83(5):699-709; Scholey A B, Tildesley N T, Ballard C G, Wesnes K A, Tasker A, Perry E K, Kennedy D O. An extract of *Salvia* (sage) with anticholinesterase properties improves memory and attention in healthy older volunteers. *Psychopharmacology* (Berl) 2008; 198(1):127-39), and rosemary (Pengelly A, Snow J, Mills S Y, Scholey A, Wesnes K, Butler L R. Short-term study on the effects of rosemary on cognitive function in an elderly population. *J Med Food* 2012; 15(1):10-7), may promote cognitive function in healthy volunteers. Compounds in the essential oils of plants within the Lamiaceae family, such as menthone, piperitone oxide, camphor, linalool, and polyphenols, are likely responsible for the wide range of reported biological activity of these plant extracts (Mimica-Dukic N, Bozin B, Sokovic M, Mihajlovic B, Matavulj M. Antimicrobial and antioxidant activities of three *Mentha* species essential oils. *Planta Med* 2003; 69(5):413-9; Hussain A I, Anwar F, Nigam P S, Ashraf M, Gilani A H. Seasonal variation in content, chemical composition and antimicrobial and cytotoxic activities of essential oils from four *Mentha* species. *J Sci Food Agric* 2010; 90(11):1827-36). However, randomized controlled trials specifically investigating the effects of spearmint on cognitive function are limited to a few studies which suggest spearmint-flavored chewing gum improves memory in healthy volunteers; albeit the evidence is conflicting (Baker J R, Bezance J B, Zellaby E, Aggleton J P. Chewing gum can produce context-dependent effects upon memory. *Appetite* 2004; 43(2):207-10; Tucha O, Mecklinger L, Maier K, Hammerl M, Lange K W. Chewing gum differentially affects aspects of attention in healthy subjects. *Appetite* 2004; 42(3):327-9; Miles C, Johnson A J. Chewing gum and context-dependent memory effects: a reexamination. *Appetite* 2007; 48(2):154-8; Johnson A J, Miles C. Chewing gum and context-dependent memory: the independent roles of chewing gum and mint flavour. *Br J Psychol* 2008; 99(Pt 2):293-306).

Currently, spearmint is widely used as an additive in beverages and confectioneries and has Generally Recognized as Safe (GRAS) status as a natural seasoning/flavoring, essential oil, or natural extract in the United States (FDA 2012a. Substances generally recognized as safe: Essential oils, oleoresins (solvent-free), and natural extractives (including distillates). 12CRF182.20; FDA 2012b. Substances generally recognized as safe: Spices and other natural seasonings and flavorings. 12CRF182.10). However, the safety and tolerability of spearmint in humans when consumed at doses higher than what would typically be consumed as a flavoring or seasoning has not previously been evaluated.

BRIEF SUMMARY OF THE INVENTION

Current cognitive health products have only shown benefit in acute, cross-over study, and have inconsistent findings. Thus, there is a need for natural botanical extracts with proven efficacy following chronic supplementation. The inventions described herein relate to the administration of an extract of plants of the Lamiaceae family that contain rosmarinic acid, and have a positive impact on overall cognitive health, including improvements in memory, reasoning, attention/concentration, planning, mood, sleep and associated behaviors.

BRIEF DESCRIPTION OF THE DRAWINGS

FIG. 1 presents a chart of the quality of working memory scores during 90 day supplementation with spearmint extract.

FIG. 2 presents a chart of spatial working memory distractor items correctly identified during 90 day supplementation with spearmint extract.

DETAILED DESCRIPTION OF THE INVENTION

The inventions described herein relate generally to plant extracts that enhance, improve or sustain cognitive health and function and, more specifically, to the administration of an extract of a plant of the Lamiaceae family, including the *Mentha* genus, such as spearmint (*Mentha spicata* L.) comprising rosmarinic acid, which has surprisingly shown an improvement in memory, reasoning, attention/concentration, planning, mood, sleep and associated behaviors.

Definitions

To facilitate understanding of the disclosure, the following definitions are provided:

As used herein, the terms "administering," "administered" and "administration" refer to any method of providing a composition or extract to a mammal. Such methods are well known to those skilled in the art and include, but are not limited to, oral administration, transdermal administration, administration by inhalation, nasal administration, and topical administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

Cardiovascular health or vascular health refers to systemic brachial blood pressure, aortic blood pressure, heart rate, wave reflection, systolic blood pressure, augmentation index, diastolic blood pressure or aortic/arterial stiffness evaluation. Cardiovascular assessments also refer to blood oxygenation levels, cerebral metabolic rate of oxygen, cerebral blood flow, cerebral cellular energy.

Cognitive health refers to the health of the overall brain, tissues and blood supply as well as its' ability to function appropriately under various conditions. Good cognitive health is vital for the brain to perform all mental processes; collectively known as cognition including, but not limited to, learning, intuition, judgment, language, attention (simple, complex, sustained), alertness, focus and memory (both long and short-term); at peak performance. Poor cognitive health due to aging, diseases and/or other cognitive detriments reduce the brain's ability to function appropriately resulting in significant declines in cognitive function and performance.

Cognitive function refers to any mental or intellectual process involving neurological or symbolic operations including, but not limited, to communication, perception, comprehension, reasoning, memory, thinking, awareness, speed of thinking, focus, concentration, attention, alertness, motivation, drawing conclusions, executive function, attention, episodic memory, executive function, working memory, letter-number sequencing and cancellation, processing speed (COMPASS & Weschler), motor/psychomotor speed, creation of imagery, creativity, capacity for judgment, finger tapping, symbol digit coding, Stroop test, shifting attention test, continuous performance test, non-verbal reasoning test, and 4-part continuous performance test, language, visuoconstructional skills, conceptual thinking, calculations, orientation, word presentation, immediate word recall, picture presentation, reaction time (simple and choice), digit vigilance, digit span, numeric working memory, spatial working memory, delayed word recall, word recognition, picture recognition, tracking, and executive function. In animal model systems, cognitive function may be measured in various conventional ways known in the art, including using a Morris Water Maze (MWM), Barnes circular maze, elevated radial arm maze, T-maze or any other mazes in which the animals use spatial information. Other tests known in the art may also be used to assess cognitive function, such as novel object recognition, foot lever press, and odor recognition tasks.

Executive Function refers to cognitive processes that regulate, control, and manage other cognitive processes, such as planning, working memory, attention, problem solving, verbal and non-verbal reasoning, mathematical ability, inhibition, mental/cognitive flexibility, task switching, initiation, flexibility, visual attention, math skills, adaptability to new and changing environments and monitoring of actions.

Learning refers to the act, process, or experience of gaining knowledge or skill; psychological or behavioral modification especially through experience or conditioning.

Memory refers to the collection of information gained from past learning or experience that is stored in a person's mind. A piece of information, such as the mental image of an experience, that is stored in the memory. The ability to remember past experiences or learned information, involving advanced mental processes such as learning, retention, recall, and recognition and resulting from chemical changes between neurons in several different areas of the brain, including the hippocampus. Included are (1) declarative learning or memory, which refers to which can be consciously recalled such as facts and knowledge, (2) working memory, which refers to actively holding multiple pieces of transitory information in the mind where they can be manipulated, (3) reference memory, which refers to information gained from previous experience, either recent or remote, (4) recognition memory, which is the ability to recognize previously encountered events, objects, or people, (5) associative memory, which is the ability to learn and remember the relationship between unrelated items, (6) episodic memory, which is memory of autobiographical events (times, places, associated emotions, and other contextual who, what, when, where, why knowledge) that can be explicitly stated, (7) secondary memory, which is the ability to recall information after an increment of time has passed, whether recent or more remote (hours, days, months or years), but in either case some distractions have occurred for the individual from time the information was first learned. Each of these has an immediate, short-term, and long-term component. Immediate memory lasts for just a few seconds. Short-term memory stores information that has been minimally processed and is available only for a few minutes, as in remembering a phone number just long enough to use it. Short-term memory is transferred into long-term memory, which can last for many years, only when repeated use of the information facilitates neurochemical changes that allow it to be retained. Long term memory is used interchangeably with secondary memory.

Mood refers to, but is not limited to, tension, anxiety, calmness, depression, dejection, anger, hostility, vigor, activity, energy, fatigue, lethargic, inertia, confusion, bewilderment, mood disturbance, contentedness, tranquil, troubled, relaxed, happiness, sadness, withdrawn, sociable, friendly, incompetent, proficient, total mood disturbance.

Polyphenols are widely distributed in plants and play a protective role in defense against environmental stresses, such as temperature extremes, ultraviolet radiation or pathogens. Polyphenols are divided into different classes of compounds according to the number of phenol rings they contain and the structure of the linkage of these rings. Recent studies have suggested a role for polyphenols in disease prevention and health promotion through dietary intake.

The phrase "quality of life" refers to the satisfaction with aspects of life, including health, physical and emotional function, activities of daily living, psychological wellbeing, spiritual wellbeing, social wellbeing, economic wellbeing, and family contentment, Sleep refers to ease of getting to sleep, quality of sleep, awakening from sleep, ease of awakening from sleep, alertness upon wakening, behavior following wakening, balance, coordination, duration of sleep, disturbances in sleep, sleep latency, daily dysfunction due to sleepiness, sleep efficiency, use of medications to sleep, global Pittsburgh sleep quality index score.

Stressful conditions refer to events that occur leading to stress (i.e., worry, anxiety, and negative effects on mental and physical well-being, or a condition that results in a disturbance in physical or mental equilibrium). Sleep-associated stressful conditions include but are not limited to those conditions characterized by a disruption of circadian rhythms, such as jet lag, time zone changes, pregnancy, medications, changes in routine and shift work.

As used herein, therapeutically effective amount or efficacious amount refers to the amount of a compound or composition or derivatives thereof of the present invention is an amount that, when administered to a subject, will have the intended therapeutic effect. The full therapeutic effect does not necessarily occur by administration of one dose, and may occur after administration of a series of doses. Thus, a therapeutically effective amount may be administered in one or more administrations. The precise effective amount needed for a subject will depend upon, for example, the subject's size, health and age, the nature and extent of the cognitive impairment, and the therapeutics or combination of therapeutics selected for administration, and the mode of administration. In one embodiment, the at least one extract of a plant of the Lamiaceae family as described herein are for administration, for example, RA, on a daily frequency or more than once a day, for instance two, three, or four times a day.

The use of the word treatment or treating refers to clinical intervention in an attempt to alter the natural course of the individual, animal or cell being treated, and may be performed either for prophylaxis or during the course of clinical pathology. Desirable effects include preventing occurrence or recurrence of disease, alleviation of symptoms, and diminishment of any direct or indirect pathological consequences of the disease, lowering the rate of disease progression, amelioration or palliation of the disease state, and remission or improved prognosis. A condition or subject refers to taking steps to obtain beneficial or desired results, including clinical results. Beneficial or desired clinical results include, but are not limited to, enhancing, improving or sustaining cognitive health and/or function, alleviation or amelioration of one or more symptoms associated with mild cognitive impairment, or age-related cognitive impairment, delay or slowing of that impairment, amelioration, palliation or stabilization of that impairment, and other beneficial results, such as improvement of cognitive function or a reduced rate of decline of cognitive function in subjects with age-related cognitive impairment or at risk thereof. In at least one embodiment, these terms include the prevention or treatment of cognitive disorders such as dyslexia, aspraxia, attention-deficit-hyperactivity disorder, attention-deficit disorder autism, Alzheimers, Parkinsons or stroke, or other disorders of executive function.

As used herein, the singular forms "a," "an," and "the" include plural referents unless the context clearly dictates otherwise. Thus, for example, reference to "a factor" refers to one or mixtures of factors, and reference to "the method of treatment" includes reference to equivalent steps and methods known to those skilled in the art, and so forth.

Before explaining the various embodiments of the disclosure, it is to be understood that the invention is not limited in its application to the details of construction and the arrangement of the components set forth in the following description. Other embodiments can be practiced or carried out in various ways. Also, it is to be understood that the phraseology and terminology employed herein is for the purpose of description and should not be regarded as limiting the inventions described in any way.

Throughout this disclosure, various publications, patents and published patent specifications are referenced. Where permissible, the disclosures of these publications, patents and published patent specifications are hereby incorporated by reference in their entirety into the present disclosure to more fully describe the state of the art.

As described herein, one aspect of the present invention includes a method to enhance, improve or sustain cognitive health and/or function in mammals, comprising administering an efficacious amount of an extract of a plant of the Lamiaceae family, wherein the primary active ingredients are rosmarinic acid and plant polyphenols. According to at least one embodiment, the extract further comprises plant polyphenols, such as carnosic acid.

Another aspect of the present invention includes a method to treat or prevent a decline in cognitive health and/or function in mammals, comprising administering an efficacious amount of an extract of a plant of the Lamiaceae family, wherein the primary active ingredients are rosmarinic acid and plant polyphenols.

In at least one embodiment of the present invention, the administration of the extract improves learning, executive function, memory, mood, or sleep. In at least one embodiment of the present invention, the administration of the extract improves quality of life.

Further aspects of the present invention include methods for improving mood in mammals, including improvements in vigor, activity, energy, or alertness. In at least one embodiment of the present invention, administration of the extract results in improved vigor, activity, energy or alertness occurs in the absence of increased depression, dejection, fatigue, or lethargy. Mood can be measured according to standards understood by those of ordinary skill, including but not limited to POMS.

In another aspect, the present invention includes a method for improving sleep in mammals, including but not limited to improvement in sleep quality, improved ability to fall asleep, a reduction in sleep disruption, and improved behavior following wakefulness. For instance, in at least one embodiment, administration of the extract reduces sleep latency.

In another aspect of the present invention, the administration of the extract protects against stress induced impairment of cognitive function under a stressful condition, including but not limited to sleep associated stressful conditions. Sleep can be measured according to standards understood by those of ordinary skill, including but not limited to LSEQ.

According to at least one embodiment, the extract comprises at least 8% rosmarinic acid by weight. In a further embodiment, the extract is from a plant yielding at least 8% rosmarinic acid on a dry weight basis, including those described in U.S. patent Ser. Nos. 13/367,888 and 13/367,863, which are incorporated in their entirety by reference herein.

According to at least one embodiment, the extract is administered in an amount ranging between 0.01 and 50 mg/kg/day. In another embodiment, the extract is administered as an oral dose in the range of 600 to 900 mg/day. In one embodiment the extract is administered at regular intervals, including at least one dose per day, but in alternative embodiments includes multiple doses per day, such as two, three or four doses per day.

According to at least one embodiment, the extract is administered over the course of at least 45 days. In another embodiment, the extract is administered over the course of at least 90 days. Further still, other embodiments comprise the chronic administration of the extract.

In another aspect of the present invention, the extract is administered to humans. In another embodiment, the extract is administered to companion animals, such as cats and dogs.

EXAMPLE 1

An efficacy study was conducted on the spearmint extract in order to evaluate its potential in improving learning and memory in a SAMP8 mouse model of accelerated aging (U.S. patent application Ser. No. 13/962,609, filed Aug. 8, 2013, and incorporated herein by this reference). SAMP8 mice were administered spearmint extract or vehicle control. In addition, a 50% SAMP8 backcross strain served as the control which also received vehicle. After 90 days of treatment mice were tested in 3 behavioral tests which included, T-maze foot shock avoidance, object recognition and lever press. The spearmint extract improved acquisition (at both 16 and 32 mg of active/kg body weight) and retention (at all doses) in T-maze. In addition, spearmint with rosmarinic acid improved object recognition at 16 and 32 mg/kg body weight. The mouse doses of 16 and 32 mg of active/kg body weight correlate to a human equivalent dose of 91-180 mg rosmarinic acid, or 600-1200 mg of spearmint extract containing approximately 15% of the active. The results indicated that the extracts from spearmint have beneficial effects on deficits in learning and memory that occur with age in SAMP8 mice.

Safety studies were conducted on the spearmint extract (spearmint extract containing 15.4% [w/w] of rosmarinic acid) at Vanta Biosciences (Chennai, India) following the OECD and the FDA Redbook 2000 guidelines. The studies conducted included the Ames bacterial reverse mutation assay, chromosomal aberration induction assay, and 14-d and 90-d oral gavage toxicity study. Genotoxicity testing results demonstrate that spearmint extract was non-mutagenic at concentrations up to 5000 µg/plate as measured by the Ames bacterial reverse mutation assay. In addition, the spearmint extract did not demonstrate chromosomal aberration induction potential (non-clastogenic) at dose levels up to 5000 µg/ml.

Daily oral administration of the spearmint extract to male and female Sprague Dawley rats at doses up to 600 mg rosmarinic acid/kg body weight/day for 14 days was well tolerated. No test item-induced adverse effects were detected. The "No Observed Adverse Effect Level (NOAEL)" for the test item under the testing conditions was found to be 3896.1 mg/kg body weight/d of the spearmint extract. A follow-up 90-day study utilizing oral administration of the spearmint extract to male and female Sprague Dawley rats at doses up to 1948 mg rosmarinic acid/kg body weight/day for 90 d was well tolerated. The "No Observed Adverse Effect Level (NOAEL)" for the test item under the testing conditions and doses employed was found to be 300 mg rosmarinic acid/kg body weight/day (corresponding to 1948.2 mg/kg body weight/day of the spearmint extract). Utilizing a 100-fold safety factor this correlates to a human equivalent dose of 19.48 mg spearmint extract/kg body weight/day or a 1364 mg spearmint extract dose for a 70 kg human.

EXAMPLE 2

In a randomized, double-blind, placebo-controlled study, the effects of spearmint extract was evaluated on measures of cognitive performance, sleep, mood, and tolerability in men and women with age-associated memory impairment (AAMI). The objective of this trial was to evaluate the acute and chronic effects of two doses (600 mg or 900 mg) of a proprietary spearmint extract on aspects of cognitive function in men and women with AAMI.

Method:

Participants (N=90; 67% female; age=59.4±0.6 y) were randomly assigned (n=30/group) to consume 900, 600, or 0 mg/day spearmint extract for 90 days. A computerized assessment for cognitive performance, subjective cognition, mood, and sleep were completed on days 0, 45, and 90. Fasting blood samples, vital signs, and adverse events were collected to assess tolerability.

Results:

In the current study, the quality of working memory and spatial working memory accuracy improved following supplementation with 900 mg/day spearmint extract by 11% (P=0.0469) and 7.4% (P=0.0456), respectively, versus placebo. Participants that consumed 900 mg/day spearmint extract reported improvement in their ability to fall asleep, relative to participants consuming placebo (P=0.0046). Additionally, overall treatment effects were evident for vigor-activity (P=0.0399), total mood disturbance (P=0.0374), and alertness and behavior following wakefulness (P=0.0415). There were no significant differences between treatments in subjective cognition after 90 days of supplementation. No serious adverse events or clinically relevant findings were observed in any tolerability parameters. These results suggest the spearmint extract was well-tolerated and is beneficial for cognitive health and well-being in older subjects with AAMI.

Study Design Overview:

The double-blind, placebo-controlled, parallel study included one telephone screen, two screening visits (days −14 and −7), a baseline visit (day 0), and two treatment visits (days 45 and 90). Subjects were randomly assigned one of three treatments: 600 mg spearmint extract, 900 mg spearmint extract, or placebo, which was consumed each day with breakfast over a 90-day treatment period. During baseline and treatment visits (days 0, 45, and 90), subjects completed the CDR System™ computerized cognitive function test battery, computerized Bond-Lader Visual Analog Scales (VAS) of Mood and Alertness, computerized Profile of Moods States (POMS; days 0 and 90 only; at −0.75 h), computerized Leeds Sleep Evaluation Questionnaire (LSEQ; days 0 and 90 only; at −0.75 h), and the computerized Subjective Global Impression Scale of Cognition Questionnaire (SGI; day 90 only; at −0.75 h). Following their pre-dose assessments, subjects consumed a standardized breakfast and one dose of their assigned study product (0 h). Subjects also completed the computerized CDR System™ test battery and Bond-Lader VAS at 0.5, 2, 4, and 6 h post-dose.

Population Descriptions and Baseline Characteristics:

Participants were recruited to the clinic (Biofortis Innovation Services, Chicago, Ill.) between Aug. 2013 and Jan. 2014. In total, 198 subjects were screened and 90 eligible subjects were randomized to treatment constituting the ITT population. Men and women with AAMI were randomly assigned to one of three treatments, 0 (placebo), 600 mg/day, or 900 mg/day spearmint extract (N=90; n=30/group). Of the 90 subjects randomized, 3 subjects did not complete the final study visits (early termination). The three subjects that did not complete the study withdrew due to adverse events including knee pain, myalgia, headache, worsening of oily scalp, cystic acne, and heartburn. All adverse events were deemed "not related" with the exception of heartburn, which was deemed "probably related" to study product consumption.

Baseline characteristics of the subjects are presented in Table 1. The mean age of the population was 59.4±0.6 y with a mean body mass index (BMI) of 26.9±0.4 kg/m2. The majority of subjects were non-Hispanic white (90%) and female (67%). Mean baseline scores for the Memory Assessment Clinic Scale Questionnaire (MAC-Q), Mini-Mental State Exam (MMSE), and Verbal Paired Associates (VPA) I and II were 29.2±0.3 points, 28.5±0.2 points, 23.7±0.7 points, and 7.0±0.2 points, respectively. In addition, compliance with study product consumption over the 90-day supplementation period was 98.1±0.9%, 99.1±0.8%, and 100.1±0.4% for the placebo, 600 mg/day spearmint extract, and 900 mg/day spearmint extract groups,

TABLE 1

Baseline characteristics of subjects in the intent-to-treat population

|  | Overall | Placebo | 600 mg spearmint extract | 900 mg spearmint extract | P-value[1] |
|---|---|---|---|---|---|
|  | n (%) | | | | |
| Gender |  |  |  |  | 0.458 |
| Male | 30 (33) | 9 (30) | 8 (27) | 13 (43) |  |
| Female | 60 (67) | 21 (70) | 22 (73) | 17 (57) |  |
| Ethnicity |  |  |  |  | 0.613 |
| Hispanic/Latino | 5 (6) | 1 (3) | 1 (3) | 3 (10) |  |
| Non-Hispanic/Latino | 85 (94) | 29 (97) | 29 (97) | 27 (90) |  |

TABLE 1-continued

Baseline characteristics of subjects in the intent-to-treat population

|  | Overall | Placebo | 600 mg spearmint extract | 900 mg spearmint extract | P-value[1] |
|---|---|---|---|---|---|
| Race |  |  |  |  | 0.345 |
| Non-Hispanic White | 81 (90) | 27 (90) | 25 (83) | 29 (97) |  |
| Black/African American | 8 (9) | 3 (10) | 4 (13) | 1 (3) |  |
| Asian/Pacific Islander | 1 (1) | 0 (0) | 1 (3) | 0 (0) |  |
|  |  | Mean (SEM) |  |  |  |
| Age (years) | 59.4 (0.6) | 58.2 (1.2) | 59.1 (1.0) | 60.8 (1.0) | 0.248 |
| Body mass index (kg/m$^2$) | 26.9 (0.4) | 25.9 (0.7) | 27.1 (0.7) | 27.9 (0.7)[2] | 0.137 |
| MAC-Q score | 29.2 (0.3) | 29.1 (0.6) | 29.2 (0.6) | 29.1 (0.5) | 0.970 |
| MMSE score | 28.5 (0.2) | 28.5 (0.3) | 28.6 (0.3) | 28.3 (0.3) | 0.475 |
| VPA I score | 23.7 (0.7) | 23.2 (1.4) | 24.2 (1.3) | 23.8 (0.9) | 0.889 |
| VPA II score | 7.0 (0.2) | 7.0 (0.3) | 6.6 (0.4) | 7.2 (0.3) | 0.519 |

Abbreviations:
MAC-Q, Memory Assessment Clinic Scale Questionaire;
MMSE, Mini-Mental State Exam;
SEM, standard error of the mem;
VPA, Verbal Paired Associates.
[1]P-vales for the overall comparison were generated from an analysis of variance model without adjustments for multiple comparisons (n = 30/group and as overall N = [M]).
[2]Although the overall comparison of all three groups was not significant, body mass index (placebo vs. 900 mg/day spearmint extract) did reach significance (p = 0.043).

respectively. There were no differences in compliance between treatments over the 90-day period.

Results from Cognitive Performance Outcomes:

The computerized test battery from Bracket (CDR System™) was utilized for the assessment of acute and chronic effects of supplementation. When evaluated following acute administration, there were no significant main effects or interactions identified in the composite scores from CDR cognitive function tasks. A limited number of the individual cognitive function task measures showed significant main effects upon evaluation of the acute analyses over days 45 and 90; no significant effects were evident in the acute analysis at Day 0. The analysis is referred to as acute at Day 0, 45, and 90; however, subjects completed chronic administration prior to acute dosing at Day 45 and 90, thus the Day 45 and Day 90 data could be considered acute-on-chronic. The overall model for choice reaction time did reach significance in the acute analysis at Day 45 (P=0.0296). Pairwise comparisons indicate impairment only at 2 hours post-supplementation, in both the 900 and 600 mg/day spearmint extract groups, relative to placebo (P=0.0015 and P=0.0065), respectively. An overall effect in numeric working memory was also evident in both groups that consumed spearmint extract following acute dosing at Day 90 (P=0.0296). Pairwise comparisons indicate improvement at 6 hour post-supplementation in the 600 mg/day spearmint extract group, relative to placebo (P=0.0434).

Following chronic administration, an overall cognitive performance treatment effect was identified for quality of working memory in subjects supplemented for 90 days with spearmint extract (P=0.0435; FIG. 1). Pairwise comparisons of the change from baseline indicate quality of working memory improved in the 900 mg/day spearmint extract group relative to both the 600 mg/day spearmint extract (P=0.0212, Cohen's d effect size [d]=0.546) and placebo groups (P=0.0469, d=0.473), respectively. This improvement over the 90-day supplementation period was 22% in the 900 mg/day group compared to 5% and 7% in the 600 mg/day and placebo groups, respectively. In addition, subjects supplemented for 90 days with spearmint extract had an overall treatment effect in spatial working memory (distractor items correctly identified, P=0.0373; FIG. 2). This improvement from baseline was significantly greater for subjects consuming 900 mg/day (17%) than subjects consuming either the 600 mg/day (3%, P=0.0172, d=0.563) or placebo (6%, P=0.0456, d=0.483) over the supplementation period of 90 days.

Although spatial working memory contributes to the overall quality of memory composite, which also incorporates tasks evaluating word recognition, word recall, and picture recognition, significant differences between treatments in these factors were not evident. In addition, there were no statistically significant differences between groups in subjective cognition (SGI), power of attention, continuity of attention, speed of memory, or quality of episodic secondary memory factors or their contributing individual cognitive tasks following 90 days of supplementation.

TABLE 2

Subjective ratings of mood, from the Profile of Mood States questionnaire, before and after 90 days of supplementation with * spearmint extract.[1]

|  | Placebo | | 600 mg spearmint extract | | 900 mg spearmint extract | |  |
|---|---|---|---|---|---|---|---|
|  | Day 0 | Day 90 | Day 0 | Day 90 | Day 0 | Day 90 |  |
| Mood Factors | | | Mean Rating (SEM) | | | | P-value[2] |
| Tension-Anxiety | 3.53 (0.53) | 3.48 (0.51) | 4.13 (0.59) | 4.39 (0.95) | 6.10 (0.89) | 5.04 (0.62) | 0.3411 |
| Depression-Dejection | 1.80 (0.42) | 2.10 (0.59) | 1.30 (0.48) | 2.11 (0.66) | 3.83 (1.14) | 2.32 (0.79) | 0.0862 |
| Anger-Hostility | 0.73 (0.35) | 0.86 (0.28) | 0.53 (0.27) | 1.25 (0.54) | 2.07 (0.58) | 1.54 (0.48) | 0.1935 |
| Vigor-Activity | 17.47 (1.26) | 18.07 (1.30) | 16.80 (1.42) | 16.11 (1.66) | 15.90 (1.27) | 19.82 (1.17)[3] | 0.0399 |

TABLE 2-continued

Subjective ratings of mood, from the Profile of Mood States questionnaire,
before and after 90 days of supplementation with spearmint extract.[1]

| | Placebo | | 600 mg spearmint extract | | 900 mg spearmint extract | | |
| --- | --- | --- | --- | --- | --- | --- | --- |
| | Day 0 | Day 90 | Day 0 | Day 90 | Day 0 | Day 90 | |
| Mood Factors | | | Mean Rating (SEM) | | | | P-value[2] |
| Fatigue-Inertia | 3.40 (0.84) | 3.79 (0.93) | 2.50 (0.51) | 3.75 (0.79) | 4.30 (0.68) | 3.86 (0.79) | 0.2111 |
| Confusion-Bewilderment | 5.63 (0.67) | 5.10 (0.73) | 4.40 (0.43) | 4.32 (0.53) | 5.37 (0.63) | 5.00 (0.67) | 0.8448 |
| Total Mood Disturbance | 2.87 (1.93) | 3.38 (2.58) | 1.87 (1.50) | 6.07 (2.85) | 10.60 (3.49) | 5.04 (2.28)[4] | 0.0374 |

Abbreviations: SEM, standard error of the mean.
[1]The Profile of Mood States (POMS ™ Standard Form) questionnaire (65-item) was administered at baseline (day 0) and after 90 days of spearmint extract or placebo supplementation. Subjects were asked to rate how they have been feeling in the last week as follows: not at all (0), a little (1), moderately (2), quite a bit (3), extremely (4).
[2]P-values for the overall and pairwise comparisons in the intent-to treat sample were generated from a mixed model repeated measures analysis of variance model based on the difference from baseline in mood ratings (n = 28-30/group).
[3]900 mg/day spearmint extract vs. placebo, P = 0.0646; 900 mg/day spearmint extract vs 600 mg/day spearmint extract, P = 0.0149.
[4]900 mg/day spearmint extract vs. placebo, P = 0.0832; 900 mg/day spearmint extract vs 600 mg/day spearmint extract P = 0.0123.

Results from Mood Outcomes:

Administration of the computerized Profile of Mood States (POMS) questionnaire identified significant treatment effects in the vigor-activity factor (P=0.0399, Table 2) following 90 days of supplementation with spearmint extract. The vigor-activity factor includes responses to eight adjectives which reflect feelings including active, energetic, lively, and alert. Comparison of treatment groups identified a trend for improvement over the 90-day supplementation in subjects supplemented with 900 mg/day spearmint extract in comparison to placebo-treated subjects (P=0.0646, d=0.502); while a significant (P=0.0149, d=0.729) effect was evident for subjects administered the 900 mg/day vs. 600 mg/day dose level of spearmint extract.

An effect of treatment was also evident in the overall model for TMD, obtained from all 65 questions on the POMS (P=0.0374). Consistent with the findings for the vigor-activity factor, there was a trend for improvement over the 90-day supplementation period in TMD in subjects supplemented with 900 mg/day of spearmint extract compared to subjects consuming placebo (P=0.0832, d=0.443); while, a significant (P=0.0123, d=0.621) improvement was observed for subjects consuming the 900 mg/day vs. 600 mg/day dose level of spearmint extract. Further investigation by incorporation of age and MMSE into the post-hoc covariate model showed that 90 days of supplementation with spearmint extract resulted in an overall effect of treatment (P=0.0002); furthermore, TMD improved in the group administered 900 mg/day spearmint extract relative to both the 600 mg/day spearmint extract (P=0.0009) and the placebo groups (P=0.0176). There were no significant findings for the remaining factors evaluated in the POMS questionnaire. Analysis of mood using the Bond-Lader VAS found no acute or chronic effects of spearmint extract supplementation, relative to placebo.

Results from Sleep Outcomes:

Subjects were administered the LSEQ to evaluate getting to sleep, quality of sleep, ease of awakening from sleep, and alertness and behavior following wakefulness (Table 3). An overall treatment effect (P=0.0170) was evident in ratings of getting to sleep after 90 days of supplementation. Furthermore, between group comparisons showed that individuals consuming 900 mg/day spearmint extract had improved ability to get to sleep vs. individuals consuming placebo (P=0.0046, d=0.805). An overall treatment effect was also observed for behavior following wakefulness (P=0.0415). Between group comparisons suggest that subjects consuming spearmint extract at 900 mg/day had improved behavior following wakefulness relative to subjects consuming 600 mg/day of spearmint extract (P=0.0137). No significant differences were observed in quality of sleep or ease of awakening from sleep following supplementation with spearmint extract relative to placebo.

TABLE 3

Subjective ratings of sleep, from Leeds Sleep Evaluation Questionnaire,
before and after 90 days of supplementation with spearmint extract.[1]

| | Placebo | | 600 mg spearmint extract | | 900 mg spearmint extract | | |
| --- | --- | --- | --- | --- | --- | --- | --- |
| | Day 0 | Day 90 | Day 0 | Day 90 | Day 0 | Day 90 | |
| Sleep Factors (mm) | | | Mean Rating (SEM) | | | | P-value[2] |
| Ease of Getting to Sleep | 49.83 (0.95) | 45.48 (2.15) | 51.30 (0.87) | 50.36 (1.70) | 47.63 (0.91) | 51.11 (1.36)[3] | 0.0170 |
| Quality of Sleep | 50.27 (0.37) | 48.62 (3.20) | 50.97 (1.12) | 52.04 (2.23) | 49.83 (0.57) | 53.25 (1.98) | 0.4267 |
| Ease of Awakening from Sleep | 49.40 (0.40) | 52.69 2.84) | 48.63 (1.29) | 50.54 (2.75) | 52.10 (1.31) | 54.14 (1.76) | 0.9016 |
| Alertness and Behavior following Wakefulness | 52.20 (2.13) | 59.31 (2.89) | 55.03 (2.64) | 53.50 (3.44)[4] | 52.07 (1.83) | 63.46 (2.78) | 0.0415 |

Abbreviations: SEM, standard error of the mean.
[1]The Leed's Sleep Evaluation Questionnaire was administered at baseline (day 0) and after 90 days of spearmint extract or placebo supplementation. Subjects were asked to rate aspects of sleep using 100 mm visual analog scales flanked with antonyms (i.e., a rating of 50 mm is neutral).
[2]P-values for the overall and pairwise comparisons in the intent-to-treat sample were generated from a mixed model repeated measures analysis of variance model based on the difference from baseline in ratings of sleep (n = 28-30/group).
[3]900 mg/day spearmint extract vs. Placebo, P = 0.0046; 900 mg/day spearmint extract vs. 600 mg/day spearmint extract, P = 0.0879.
[4]600 mg/day vs Placebo, P = 0.0892, 600 mg/day vs 900 mg/day sprearmint extract, P = 0.0137.

Results from Safety and Tolerance Outcomes:

Any differences identified in pre-supplementation comparability of vital signs, clinical chemistries, whole blood hematology, and lipids were within normal ranges and not clinically significant. The change from pre-supplementation was also evaluated for all measures of tolerance following 90 days of supplementation. There were no significant differences between all treatment groups over the 90-day supplementation period. Although, the overall model was not significant, any within group and between group differences in vital and clinical chemistry measures remained within normal ranges. Finally, there were no significant differences between treatment groups in the number of subjects reporting adverse events (P=0.791) or adverse events that were likely related to study product consumption (P=0.692). No events were considered serious or severe.

Conclusions:

The data indicates that the proprietary aqueous spearmint extract containing high rosmarinic acid was well-tolerated in older subjects with AAMI. Further, chronic supplementation for 90 days with 900 mg/day resulted in improved quality of working memory and spatial working memory versus placebo. As discussed earlier, working memory pertains to the ability to use and manipulate information stored within short-term memory. The study results indicated an improvement in quality of working memory and spatial working memory of approximately 15 and 9% over placebo, respectively. Self-reported cognition findings did not corroborate these objective findings. However, based on the results from the objective measures, chronic administration of the aqueous spearmint extract could potentially prevent the decline in working memory equivalent to that lost in one decade of life.

Participants also reported improvement in their ability to fall asleep. Subjective mood assessments indicate improved vigor-activity and total mood disturbance, which may likely be attributed to supplementation with 900 mg/day spearmint extract. The study results showed a surprising difference in sleep ratings following 90 days of spearmint extract supplementation at 900 mg/day that was 7.8 mm greater than ratings in the placebo group, corresponding to changes reported after use of common sleep aids (Zisapel and Nir 2003). The results of this study indicate a positive impact on cognitive health, where subjects reported improvements in working memory, mood ratings, for instance improved vigor-activity and total mood disturbance, and improvement in sleep, for instance improved ability to fall asleep at night and improved behavior following wakefulness.

The strengths of the current study include use of a randomized, double-blind, placebo-controlled study design, thus reducing confounding by baseline variables and interventions and potential bias by the subject and investigators. Compliance with study product consumption was greater than 98% in all groups. The CDR System™ computerized testing battery has been used in numerous clinical trials, validated for populations with AAMI, and has been shown to be sensitive to acute and chronic nutraceutical supplementation. The computerized tests were utilized in a parallel format to reduce learning effects and all groups had training sessions to allow acclimation to the testing battery. In addition, all tools utilized for data collection were validated in this population and completed in a supervised environment where lighting and noise were controlled.

Limitations of this study include the use of free living subjects and confounding by factors such as diet and lifestyle are possible; however, subjects were asked maintain their habitual diet, exercise routines, and maintain consistent sleep duration the evening before study visits and throughout the study. In studies utilizing computerized cognitive function test batteries for evaluation of neutraceutical interventions, a majority of these are crossover in design which may be better suited for evaluation of acute effects and may explain our lack of acute findings in the current trial. Evaluation of outcomes measured at multiple time points on each test day including the objective cognitive measures and mood assessed by the Bond-Lader, utilized average daily values. One criticism of this approach is that utilization of daily averages at the baseline visit may allow any acute effects from the pre-dose assessment to confound the chronic analysis. However, there were no between group differences at the baseline visit between pre-dose and post-dose visits. Therefore, the differences measured and reported within this study best reflect what an individual might expect following a chronic dosing regimen.

For the first time, this research demonstrates the effects of an aqueous spearmint extract on cognitive function following chronic administration in a parallel design. The results of this randomized, double-blind, placebo-controlled trial suggests that the spearmint extract was well-tolerated with chronic supplementation. Administration of 900 mg/day of an aqueous spearmint extract containing high rosmarinic acid improved working memory, and further still, showed positive effects regarding mood and sleep in older subjects with AAMI. Additionally, the data suggests that administering plant extracts as described herein has a positive impact on overall cognitive health and/or function, including improvements in memory, reasoning, attention/concentration, planning, mood, sleep and associated behaviors. The data supports use of this distinct aqueous spearmint extract as a nutritional intervention for cognitive health and well-being.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

We claim:

1. A method for improving sleep in a mammal in need thereof comprising administering to the subject an efficacious amount of an extract of a spearmint plant of the Lamiaceae family for a time period of at least 45 days, wherein the efficacious amount of the extract is between 0.01 and 50 mg/kg/day, wherein the primary active ingredients of said extract are rosmarinic acid and plant polyphenols and wherein said extract comprises at least 8% rosmarinic acid by weight.

2. The method of claim 1, wherein administration of the extract reduces sleep latency.

3. The method of claim 1, wherein administration of the extract improves ability to fall asleep, quality of sleep, ease of awakening from sleep, alertness and behavior following wakefulness, duration of sleep, sleep efficiency.

4. The method of claim 1, wherein improvement in sleep is measured by LSEQ.

5. The method of claim 1, wherein improved sleep results in increased vigor, alertness and energy and decreases fatigue.

6. The method of claim 1, wherein administration of the extract improves mood as measured by POMS.

7. A method for improving sleep in a mammal in need thereof comprising administering to the subject an efficacious amount of an extract of a spearmint plant comprising the steps of administering to the mammal at least 600 mg/day spearmint extract for a time period of at least 45 days, wherein the spearmint extract contains at least 8% rosmarinic acid by weight.

8. The method of claim 7 wherein the extract is orally administered as a capsule.

9. The method of claim 1 whereby the spearmint plant extract is administered at least 90 days.

10. A method for improving sleep in a mammal in need thereof comprising administering to the subject an efficacious amount of an extract of a spearmint plant of the Lamiaceae family, wherein the efficacious amount of the extract is between 0.01 and 50 mg/kg/day, wherein the primary active ingredients of said extract are rosmarinic acid and plant polyphenols and wherein said extract comprises at least 8% rosmarinic acid by weight, and further providing that the spearmint plant extract is administered at least twice daily.

11. The method of claim 10 whereby the spearmint plant extract is administered at least three times daily.

12. The method of claim 10 whereby the spearmint plant extract is administered for a time period of at least 45 days.

13. A method for improving sleep in a mammal in need thereof comprising administering to the subject an efficacious amount of an extract of a spearmint plant of the Lamiaceae family for a time period of at least 90 days, wherein the efficacious amount of the extract is between 0.01 and 50 mg/kg/day, wherein the primary active ingredients of said extract are rosmarinic acid and plant polyphenols and wherein said extract comprises at least 8% rosmarinic acid by weight.

* * * * *